US007141553B2

(12) United States Patent
Fishman

(10) Patent No.: US 7,141,553 B2
(45) Date of Patent: Nov. 28, 2006

(54) A3AR AGONISTS FOR THE TREATMENT OF INFLAMMATORY ARTHRITIS

(75) Inventor: Pnina Fishman, Herzliya (IL)

(73) Assignee: Can-Fite Biopharma Ltd. Israel, Petach Tikva (IL)

(*) Notice: Subject to any disclaimer, the term of this patent is extended or adjusted under 35 U.S.C. 154(b) by 0 days.

(21) Appl. No.: 10/715,823

(22) Filed: Nov. 19, 2003

(65) Prior Publication Data
US 2004/0167094 A1    Aug. 26, 2004

Related U.S. Application Data

(60) Provisional application No. 60/427,182, filed on Nov. 19, 2002.

(51) Int. Cl.
*A01N 43/04* (2006.01)
*A61K 31/70* (2006.01)
*C07H 19/16* (2006.01)

(52) U.S. Cl. ............... 514/46; 514/45; 536/27.22; 536/27.6; 536/27.63

(58) Field of Classification Search .............. 514/45, 514/46; 536/27.22, 27.6, 27.63
See application file for complete search history.

(56) References Cited

U.S. PATENT DOCUMENTS 5,773,423 A * 6/1998 Jacobson et al. ............. 514/45
6,323,027 B1 * 11/2001 Burkly et al. ............... 435/334

OTHER PUBLICATIONS

Baharav et al. International Journal of Molecular Medicine, (2002) vol. 10, No. Supplement 1, pp. S104, Meeting info: 7th World Congress on Advances in Oncology and the 5th International Symposium on Molecular Medicine, Hersonissos, Crete, Greece, Oct.*
Bonvini et al, "Nuclear β-Catenin Displays GSK-3β- and APC-Independent Proteasome Sensitivity in Melanoma Cells", *Biochemica et Biophysica Acta* 1495:308-318 (2000).
Fang et al, "Phosphorylation and Inactivation of Glycogen Synthase Kinase 3 by Protein Kinase A", *Proc Nat'l Acad Sci* 97(22):11960-11965 (2000).
Ferkley et al, "GSK-3: New Thoughts on an Old Enzyme", *Developmental Biology* 225:471-479 (2000).
Fishman et al, "Evidence for Involvement of Wnt Signaling Pathway in IB-MECA Mediated Suppression of Melanoma Cells", *Oncogene* 21:4060-4064 (2002).
Olah et al, "The Role of Receptor Structure in Determining Adenosine Receptor Activity", *Pharmacology & Therapeutics* 85:55-75 (2000).
Poulsen et al, "Adenosine Receptors: New Opportunities for Future Drugs", *Bioorganic & Medicinal Chemistry* 6:619-641 (1998).
Szabó et al, "Suppression of Macrophage Inflammatory Protein (MIP)-1α Production and Collagen-Induced Arthritis by Adenosine Receptor Agonists", *British Journal of Pharmacology* 125:379-387 (1998).
Baharav, Ehud, et al, "The Anti-Inflammatory Effect of A3 Asenosine Receptor Agonists in Murine Autoimmune Arthritis Models", International Journal of Molecular Medicine, v. 12, n. Supplement 1, pp. S42 (2003).
Baharav, Ehud, et al, "The Effect of Adenosine and the A3 Adenosine Receptor Agonist IB-MECA on Joint Inflammation and Autoimmune Diseases Models", International Journal of Molecular Medicine, v. 10, n. Supplement 1, pp. S104 (2002).
Fang, G., et al, "Adenosine (ADO) Agonists Protect Mice from Death in a Model of Endotoxemia by Binding to $A_{2A}$ but not $A_3$ ADO Receptors", Abstracts of the Interscience Conference on AntiMicrobial Agents and Chemotherapy, v. 41, pp. 754, (2001).
Hasko, G., et al, "Stimulation of Adenosine 3 Receptors Exerts Anti-Inflammatory Effects in Acute and Chronic Models of Inflammation", Drug Development Research, v. 43, n.1, pp. 39, (Jan. 1998).
Mabley, Jon, et al, "The A3 Adenosine Agonist, IB-MECA, Protects Against the Development of Arthritis and Reverses Established Arthritis", FASEB Journal, vol. 16, n. 5, pp. A1044, (Mar. 22, 2002).
Szabo, Csaba, et al, "Suppression of Macrophage Inflammatory Protein (MIP)-1α Production and Collagen-Induced Arthritis by Adenosine Receptor Agonists", British Journal of Pharmacology, v. 125, pp. 379-387, (1998).

* cited by examiner

*Primary Examiner*—Patrick Lewis
(74) *Attorney, Agent, or Firm*—Browdy and Neimark, PLLC

(57) ABSTRACT

The present invention concerns a method for the treatment of inflammatory arthritis, and in particular rheumatoid arthritis, by administering to the subject specific low dosages of N6-(3-iodobenzyl)-adenosine 5'-N-methyl-uronamide (IB-MECA) and 2-chloro-N6-(3-iodobenzyl)-adenosine-5'-N-methyl-uronamide (CL-IB-MECA).

4 Claims, 11 Drawing Sheets

FIG. 3A Untreated
FIG. 3B IB-MECA

FIG. 5A Untreated
FIG. 5B
FIG. 5C Cl-IB-MECA
FIG. 5D

A3AR AGONISTS FOR THE TREATMENT OF INFLAMMATORY ARTHRITIS

FIELD OF THE INVENTION

This invention relates to the field of therapeutics and in particular relates to the treatment of arthritis.

PRIOR ART

The following is a list of prior art, which is considered to be pertinent for describing the state of the art in the field of the invention. Acknowledgement of these references herein will be made by indicating the number from their list below within brackets.
(1) Olah M. E. and Stiles G. L. The role of receptor structure in determining adenosine receptor activity, *Pharmacol. There.*, 85:55–75 (2000);
(2) Poulsen S. A. and Quinn R. J., Adenosine receptors: new opportunities for future drugs. *Bioorg. Med Chem.*, 6:619–641 (1998);
(3) Fang X. et al. Phosphorylation and inactivation of glycogen synthase kinase 3 by protein kinase A., *Proc. Natl. Acad. Sci. USA*, 97:11960–11965 (2000);
(4) Fishman, P., et al., Involvement of Wnt Signaling Pathway in IB-MECA Mediated Suppression of Melanoma Cells, *Oncogene* 21:4060–4064 (2002);
(5) Ferkey, D. M., and Kimelman, D. GSK-3: New Thoughts on an Old Enzyme, *Dev. Biol.*, 225:471–479 (2000);
(6) Bonvini, P., et al. Nuclear beta-catenin displays GSK-3beta- and APC-independent proteasome sensitivity in melanoma cells, *Biochim Biophys. Acta.*, 1495:308–318 (2000);
(7) Olah, M E. and Stiles, G. L., The role of receptor structure in determining adenosine receptor activity, *Pharmacol. Ther.*, 85:55–75 (2000);
(8) Szabo C., et al. Suppression of macrophage inflammatory protein (MIP)1☐ producing and collagen induced arthritis by adenosine receptor agonists., *British Journal of Pharmacology*, 125:379–387 (1998);
(9) U.S. Pat. No. 5,773,423.

BACKGROUND OF THE INVENTION

A3 adenosine receptors belong to the family of the Gi-protein associated cell surface receptors. Receptor activation leads to its intention and the subsequent inhibition of adenylyl cyclase activity, cAMP formation and protein kinase A (PKA) expression, resulting in the initiation of various signaling pathways[1,2]. PKA contains a catalytic subunit PKAc which dissociates from the parent molecule upon activation with cAMP Recent studies have demonstrated that PKAc phosphorylates and inactivates the enzyme glycogen synthase kinase 3β (GSK-3β) [3].

Recently, it has been shown that 1-deoxy-1-[6[[(3-iodophenyl)methyl]amino]-9H-purine-9-yl]-N-methylβ-D-ribofura-nuronaminde IB-MECA) disclosed in U.S. Pat. No. 5,773,423 incorporated herein by reference, a stable agonist to A3AR, alters the expression of GSK-3β and β-catenin, key components of the Wnt signaling pathway. Consequently it let to the inhibition of the expression of the cell cycle progression genes, c-myc and cyclin D1[4].

Szabo et at, [8] reported that IB-MECA suppresses the production of MIP-1α in macrophages in a dose dependent manner, and was shown to inhibit, also in a dose dependent manner, the production of the cytokines IL-1, IL-2, IL-6 as well as NO. According to this publication, administration of 0.5 mg/kg of IB-MECA a day reduced the severity of joint inflammation in a model of collagen-induced arthritis in mice.

Rheumatoid arthritis is a common rheumatic disease, affecting more than two million people in the United States alone. The disease is three times more prevalent in women as in men but afflicts all races equally. The disease can begin at any age, but most often starts between the ages of forty and sixty. In some families, multiple members can be affected, suggesting a genetic basis for the disorder. The cause of rheumatoid arthritis is unknown. Even though infectious agents such as viruses, bacteria, and fungi have long been suspected, none has been proven as the cause. It is suspected that certain infections or factors in the environment might trigger the immune system to attack the body's own tissues, resulting in inflammation in various organs of the body. Regardless of the exact trigger, the result is an immune system that is geared up to promote inflammation in the joints and occasionally other tissues of the body, Lymphocytes are activated and cytokines, such as tumor necrosis factor/TNF and interleukin-1/IL-1 are expressed in the inflamed areas.

The clinical expression of rheumatoid arthritis is manifested by chronic inflammation of the joints, the tissue surrounding the joints such as the tendons, ligaments, and muscles, as well as other organs in the body such as the eyes. The inflammation process of causes swelling, pain stiffness, and redness in the joints. In some patients with rheumatoid arthritis, chronic inflammation leads to the destruction of the cartilage, bone and ligaments causing deformity of the joints.

SUMMARY OF THE INVENTION

The invention is described in the following SUMMARY with reference to a therapeutic method for the treatment of inflammatory arthritis. It should be noted that in addition to said therapeutic method, also encompassed within Me present invention is an oral pharmaceutical composition for the treatment of inflammatory arthritis that comprises an effective amount of the active agents as defined bellow and a carrier pharmaceutically acceptable for oral administration; as well as the use of said active agent for the preparation of a pharmaceutical composition for oral administration to a subject suffering of inflammatory arthritis and being in need for an anti-inflammatory treatment. As will be appreciated, the effective amount in the pharmaceutical composition will depend on the intended therapeutic regiment and the desired therapeutic dose. By way of example were the dose is 1 mg per day and the desired administration regiment is once daily administration, the amount of active agent in the pharmaceutical composition will be 1 mg where it is intended to divide his daily dose in 2 daily administrations, the amount of the active agent in he pharmaceutical composition will be 0.5 mg.

In the following, the term "anti-inflammatory" will be used to denote the disease modifying effect of IB-MECA or Cl-IB-MECA in alleviating the inflammatory response in inflammatory arthritis. The anti-inflammatory response may be determined on the basis of histological parameters, the extent of swollen and tender joints, motility parameters, reduction in pain, a number of different overall performance scoring systems, etc.

The present invention is based on the surprising finding that oral administration of specific A3-receptor agonists, N6-(3-iodobenzyl)-adenosine-5'-N-methyl-uronamide (IB-MECA) or 2-chloro-N$^6$-(3-iodobenzyl)-adenosine-5'-N-methyl-uronamide (Cl-IB-MECA) alleviated symptoms of inflammatory arthritis at doses which are lower than those previously described, particularly by Szabo et. al [8].

The above findings were corroborated by clinical data showing that oral administration of low doses of IB-MECA to humans led to improvements in some of the disease manifestations in rheumatoid arthritis patients.

In the following, unless otherwise indicated, dosages are indicated in weight/Kg meaning to denote weight of administered agent (IB-MECA or Cl-IB-MECA) per kilogram of body of weight in each administration: mg/Kg and microgram/Kg denoting, respectively milligrams of administered agent and micrograms of administered agent per kilogram of body weight of the treated subject.

It was also shown that the anti-inflammatory effect of these two drugs appears to be manifested with a surprising dose dependency relationship that is different than might have been expected from the prior art. In particular, it was shown that a potent anti-inflammatory activity is observed over a range of dosages without any dose clear correlation between the dose and the anti-inflammatory effect. Thus, for example, in some animal experiments an oral administration of a dose of 10 microgram/Kg had a stronger anti-inflammatory effect than a dose of 100 microgram/Kg; in some other experiments these two doses had a response that was essentially the same. Typically, pharmaceutically active substances have a classic dose-dependent effect so that the higher the dose the more pronounced the is the therapeutic effect, with the highest dose limitation being usually dictated by undesired side effects (toxicity) that become evident in higher doses. Such a classical dose-response behavior was previously reported for IB-MECA in the suppression of MIP-1 alpha production by Szabo et. al[8].

A clinician or an investigator wishing to administer IB-MECA or Cl-IB-MECA to a subject as a drug for the treatment of inflammatory arthritis or develop these drugs as a therapy for such disease would have concluded from the prior art dose-response relationship that a dose that is higher than 0.5 milligram/Kg and possibly even much higher, would be suitable for such treatment. Against this, according to the unexpected findings of the present invention, it has been demonstrated that the effect of IB-MECA and Cl-IB-MECA in the alleviation of arthritis occurs with a different dose response curve as could have been envisaged based on the prior art, as also pointed out above. According to the invention, the dose dependent curve features a very strong effect at dosages that are considerably lower than the lowest effective dose reported by Szabo et. al, with a very marked effect seen a dosages as low as 25 times lower than lowest one in the Szabo publication. This is particularly so seeing that the administration accordance with the prior art, and particularly the said Szabo publication were intraperitoneal while the administration according to the invention is oral in which case the plasma level is limited by absorption.

These findings pave the way to the development of a therapeutic regiment were effective treatment of arthritis can be achieved by administering low oral doses of IB-MECA or Cl-IB-MECA with significantly lower risk of undesired side effects.

Thus, the present invention concerns, by one embodiment, a method for the treatment of inflammatory arthritis (IA) in a human subject, comprising: orally administering to an individual in need of such treatment an effective amount of N6-(3-iodobenzyl)adenosine-5'-N-methyl-uronamide (IB-MCA) or 2-chloro-N$^6$-(3-iodobenzyl)-adenosine-5'-N-methyl-uronamide (CL-IB-MECA);

wherein the effective amount is an amount which is preferably less than the maximal tolerated dosage (MID) and is an amount in a range between $D_x$ and $D_y$; $D_x$ being an amount lower than $D_{MAX}$ and $D_Y$ being an amount higher than $D_{MAX}$; $D_{MAX}$ being an amount that yields a maximal therapeutic effect; both $D_X$ and $D_Y$ yield a therapeutic effect that is substantially less than that obtained at $D_{MAX}$.

The term "therapeutic effect that is substantially less" refers to the fact that one or more of the beneficial effects mentioned bellow in reference to the definition of "treatment" (decreased swelling, decreased pain, improved motility, slowing of the progression of the disease, increase in the time period of the remission between acute attacks of the disease, decrease in the time period of the acute attack prevention of the deterioration of the joints etc) is substantially less than that obtained at $D_{MAX}$. The term "substantially less" refers preferably to a therapeutic effect in the treatment of inflammatory arthritis (IA) that is at least about 50% of that that can be achieved with $D_{MAX}$. As can be appreciated, $D_{MAX}$ and accordingly also $D_X$ and $D_Y$, may depend on the age, gender, overall heath condition, co-administered drugs and other factors. A preferred dose is $D_{MAX}$ or a dose close to it. As may be appreciated, in practice, the effective dose may be set as an average, for example based on dose-finding clinical studies. The design of such studies is a routine undertaking of those versed in the art of clinical drug development.

The term: "inflammatory arthritis" (IA) refers in the context of the present invention to chronic inflammation, (regardless of the cause but typically due to an autoimmume process that affects the joints), in the tissue around the joints, such as the tendons, ligaments, and muscles, as well as other organs in the body. This term includes rheumatoid arthritis, psoriatic arthritis, IBD-associated arthritis, reactive arthritis, vasculities and SLE. A preferred therapy target in accordance with the invention is rheumatoid arthritis.

The term "treatment" in the context of the present invention refers to any improvement in the clinical symptoms of the disease, as well as any improvement in the well being of the patients, in particular an improvement manifested by at least one of the following: decreased swelling and tenderness of the joints, decrease in pain in the joints, improved motility, slowing of the deterioration of the joints and the surrounding tissue, increase in the remission period between acute disease attacks; decrease in the time length of the acute attack; prevention of the onset of severe disease, etc.

The effective amount in accordance with the present invention is defined as an amount that is between DX and DY, as defined above. Additionally, this amount should also be less than the maximal tolerated dosage (MTD).

The term "maximal tolerated dosage" or "MTD" refers to the highest dosage of the active substance that most people can tolerate without side effects. In accordance with clinical trials the maximal tolerated dose of IB-MCA was found to be a dose of about 5 mg (about 70 micro ram/Kg; calculated on the basis of average individual human weight of 70 Kg.) for once daily administration and a dose of about 4 mg (about 57 microgram/Kg) for twice daily administration.

The "effective amount" can be readily determined, in accordance with the invention, by administering to a plurality of tested subjects various amounts of the active agent and then plotting the physiological response (for example an integrated "arthritic index" combining several of the therapeutically beneficial effects) as a function of the amount. The amount above which the therapeutic beneficial effects begin to decrease (but is still lower than the MTS) is the "effective amount". Due to statistical distribution typically the "effective amount" is not a single parameter but a range of parameters.

In murine the effective amount is typically less than about 400 microgram/Kg. A typical dose would be in the range of about 1 microgram/Kg to about 200 microgram/Kg, with a preferred dose being in the range of about 5 microgram/Kg to about 150 microgram/Kg. The corresponding effective amount in human will be an equivalent amount to that observed in murine, which may be determined in a manner as explained bellow.

The present invention thus concerns, by another embodiment, a method for the treatment of inflammatory arthritis (IA) in a human subjetc, comprising orally administering to a mammal in need of such treatment an effective amount of $N^6$-(3-iodobenzyl)adenosine-5'-N-methyl-uronamide (IB-MECA) or 2-chloro-$N^6$-(3-iodobenzyl)-adenosine-5'-N-methyl-uronamide (CL-IB-MECA), wherein the effective amount is an amount which the human equivalent of a murine dose of 0.001 mg/Kg to 0.4 mg/Kg administered once or more, preferably twice a day.

The term "human equivalent" refers to the dose that produces in human the same effect as featured when a dose of 0.001–0.4 mg/Kg of IB-MECA or Cl-IB-MECA is administered to a mouse or a rat. As known, this dose depends and may be determined on the basis of a number of parameters such as body mass, body surface area, absorption rate of the active agents, clearance rate of the agent, rate of metabolism and others.

The human equivalent may calculated based on a number of conversion criteria as explained bellow; or may be a dose such that either the plasma level will be similar to that in the murine following administration at a dose as specified above; or a dose that yields a total exposure (namely area under the curve—AUC—of the plasma level of said agent as a function of time) that is similar to that in murine at the specified dose range.

It is well known that an amount of X mg/Kg administered to rats can be converted to an equivalent amount in another species (notably humans) by the use of one of possible conversions equations well known in the art. Examples of conversion equations are as follows:

| Conversion I: | | | |
|---|---|---|---|
| Species | Body Wt. (Kg) | Body Surf. Area (m²) | Km Factor |
| Mouse | 0.2 | 0.0066 | 3.0 |
| Rat | 0.15 | 0.025 | 5.9 |
| Human Child | 20.0 | 0.80 | 25 |
| Adult | 70.0 | 1.60 | 37 |

Body Surface area dependent Dose conversion: Rat (150 g) to Man (70 Kg) is 1/7 the rat dose. This means that in the present case 0.001–0.4 mg/Kg in rats equals to about 0.14–56 microgram/Kg in humans; assuming an average weight of 70 Kg, this would translate into an absolute dosage of about 0.01 to about 4 mg.

Conversion II:

The following conversion factors: Mouse=3, Rat=67. Multiply the conversion factor by the animal weight to go from mg/Kg to mg/m² for human dose equivalent.

| Species | Weight (Kg) | BSA (m²) |
|---|---|---|
| Human | 70.00 | 1.710 |
| Mouse | 0.02 | 0.007 |
| Rat | 0.15 | 0.025 |
| Dog | 8.00 | 0.448 |

According to this equation the amounts equivalent to 0.001–0.4 mg/Kg in rats for humans are 0.16–64 μg/Kg; namely an absolute dose for a human weighing about 70 Kg of about 0.011 to about 4.4 mg, similar to the range indicated in Conversion I.

Conversion III:

Another alternative for conversion is by setting the dose to yield the same plasma level or AUC as that achieved following administration to an animal. Based on measurement made in mice following oral administration of IB-MECA and based on such measurements made in humans in a clinical study in which IB-MECA was given to healthy male volunteers it was concluded that a dose of 1 microgram/Kg–400 microgram/KG in mice is equivalent to a human dose of about 0.14–57 microgram/Kg, namely a total dose for a 70 Kg individual of 0.01–4 mg. This is again similar to the dosages calculated according to Conversion I and II.

Based on the above conversion methods, the preferred dosage range for IB-MECA and Cl-IB-MECA would be less than 4 mg, typically within the range of about 0.01 to about2 mg (about 0.14–28 micrograms/Kg, respectively) and desirably within the range of about 0.1 to 1.5 mg (about 1.4–21 micrograms/Kg, respectively). This dose may be administered once, twice or at times several times a day. Human studies showed (data not shown herein) that the level of IB-MECA decays in the human plasma with a half life of about 8–10 hours, as compared to a half life of only 1.5 hours in mice, in case of multiple daily administration, correction in the dosages for accumulative effects needs to be made at times (a subsequent dose is administered before the level of a previous one was decayed and thus there is a build-up of plasma level over that which occurs in a single dose. On the basis of said human trials twice daily administration appears to be a preferred administration regiment. However this does not rule out other administration regiments.

The present invention discloses for the first time clinical trials in humans showing the effectiveness of IB-MECA, in a specific dosage range, in the treatment of rheumatoid arthritis. In this human study IB-MECA was administered to patients in dose ranging between 0.1 to 4 mg twice daily.

The administration of said agent to a patient may be together with a pharmaceutically carrier acceptable for oral administration.

By the term "pharmaceutically acceptable carrier" it is meant any one of inert non-toxic materials, which do not react with the IB-MECA or Cl-IB-MECA and which can be added to oral formulations as diluents or carriers or to give form or consistency to the formulation. The formulation may be in the form of a pill, capsule, in the form of a syrup, an aromatic powder, and other various forms. The carrier is selected at times based on the desired form of the formulation. The carrier may also at times have the effect of the improving the delivery or penetration of the active ingredient to the target tissue, for improving the stability of the drug, for slowing clearance rates, for imparting slow release properties, for reducing undesired side effects etc. The carrier may also be a substance that stabilizes the formulation (e.g. a preservative), for providing the formulation with an edible flavor, etc. The carriers maybe any of those conventionally used and is limited only by chemical-physical considerations, such as solubility and lack of reactivity with IB-MECA or CL-IB-MECA, and by the route of administration. The carrier may include additives, colorants, diluents, buffering agents, disintegrating agents, moistening agents, preservatives, flavoring agents, and pharmacologically compatible carriers. In addition, the carrier may be an adjuvant, which, by definition are substances affecting the action of the active ingredient in a predictable way. Typical examples of carriers include (a) liquid solutions, where an effective amount of the active substance is dissolved in diluents, such as water, saline, natural juices, alcohols, syrups, etc.; (b) capsules (e.g. the ordinary hard- or soft-shelled gelatin type containing, for example, surfactants, lubricants, and inert fillers), tablets, lozenges (wherein the active substance is in a flavor, such as sucrose and acacia or tragacanth or the active substance is in an inert base, such as gelatin and glycerin), and troches, each containing a predetermined amount of IB-MECA or CL-IB-MECA as solids or granules; (c) powders; (d) suspensions in an appropriate liquid; (e) suitable emulsions; (f) liposome formulation; and others.

The invention will now be exemplified in the following description of experiments that were carried out in accordance with the invention. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described hereinbelow.

BRIEF DESCRIPTION OF THE DRAWINGS

In order to understand the invention and to see how it may be carried out in practice, some preferred embodiments will now be described, by way of non-limiting examples only, with reference to the accompanying drawings, in which:

FIGS. 3A and 3B: show histological sections of a slice from a rat's joint having adjuvant induced arthritis: untreated (3A) and treated with 10 microgram/kg a day IB-MECA, treatment starting 7 days after disease induction (3B);

FIGS. 5A to 5D: shows pictures of rats (5A & 5C) and an enlarged picture of their paws (5B & 5D, respectively), having adjuvant induced arthritis treated (5A) and untreated (5C) with CL-IB-MECA 10 microgram/kg a day, treatment staring 7 days after disease induction;

DETAILED DESCRIPTION OF THE INVENTION

EXAMPLE 1

Experimental Procedures

Materials and Methods

IB-MECA and Cl-IB-MECA were purchased from RBI/Sigma (Natick, Mass., USA). For both reagents, a stock solution of 10 μM was prepared in DMSO and further dilutions in RPMI medium were performed.

1. Adjuvant Arthritis-Induction

Animal: Rats: LEWIS. Age: 9–12 Weeks. Sex: Female

Disease induction: 10 microgram/ml Heat killed Mycobacterium tuberculosis H37Ra (Difco, Detroit, Mich., USA) present in /IFA=Incomplete Freund's Adujvant (Sigma), were injected in an amount of 100 microliter at the tail base, S.C. (Sub Cut) In accordance with the ref: Current Protocols in Immunology ed. John E. Coligon, (1996) Unit 15.5.

2. Collagen-Induced-Arthritis

Male DBA mice, aged 10 weeks, were injected SC with 100 μl of Type II collagen 200 μg in complete Freund's adjuvant (CFA). On day 21 a booster injection of the same emulsion was administered. Mice were inspected daily for symptoms of clinical arthritis.

3. Arthritis Evaluation

The inflammatory intensity, presented as joint swelling, was measured by Caliper (Mitutoyo Co., Tokyo, Japan). Histopathological sections of these decalcified whole joints were stained with hematoxylin-eosin. Slides were screened for the following arthritic characteristics: inflammatory cell infiltration, synovial cell lining hyperplasia and pannus formation. The histological assessment of the knees inflammation intensity was divided to four parameters:

1. Lymphatic follicle like formation—graded 0–4
2. Inflammatory cells infiltration—graded 0–4
3. Synovial cells hyperplasia—graded 0–4
4. Pannus formation—graded 0–4

The arithmetic sum of these four parameters above all together designated-"Total Arthritic Score" (Goldenberg et al, J. Rheumatol. 1: 5–11, 1983). The white blood cell (WBC) count and the serum levels of the pro-inflammatory cytokine TMF-α served as humoral markers of the immune system activation. Tumor necrosis factor-α sera level was determined, in accordance with the manufacturer's guidelines, by ELISA kit "Quantikine M" (R&D Systems, Minneapolis, Minn., USA).

4. Statistical Analysis

The results were statistically evaluated using the Student's t-test. Comparison between the mean values of different experiments was carried out. The criterion for statistical significance was p<0.05.

Example 1A

Effect of 10 and 100 µg/kg IB-MECA on Inflammatory Intensity-adjuvant Model

Figure 1A:
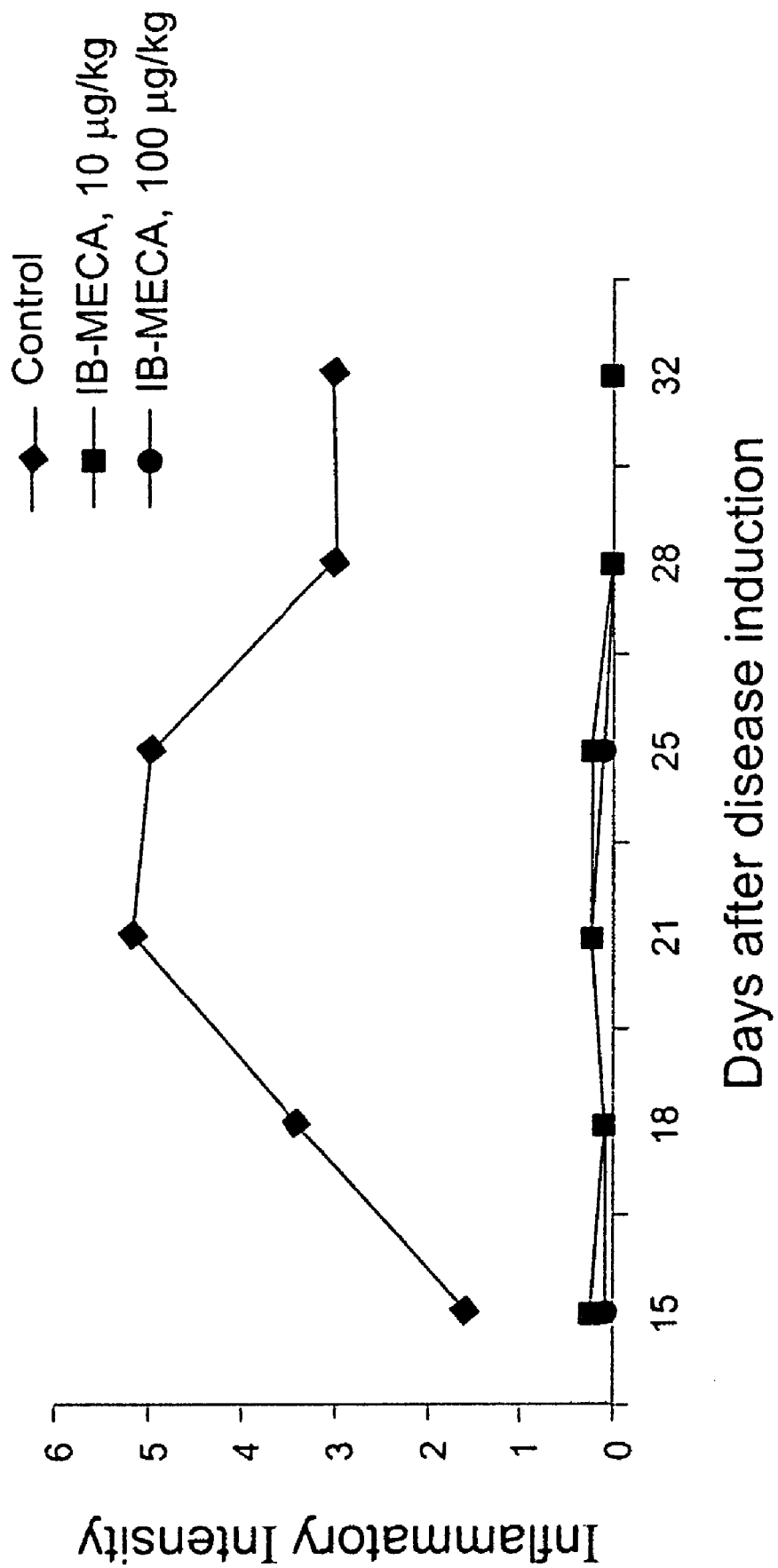
FIG. 1A: shows the effect of PO administered IB-MECA 10 microgram/kg a day (square), or 100 microgram/kg a day (circle), or control untreated mice (diamond), on the inflammatory intensity in an animal model of adjuvant arthritis.
Figure 1B:
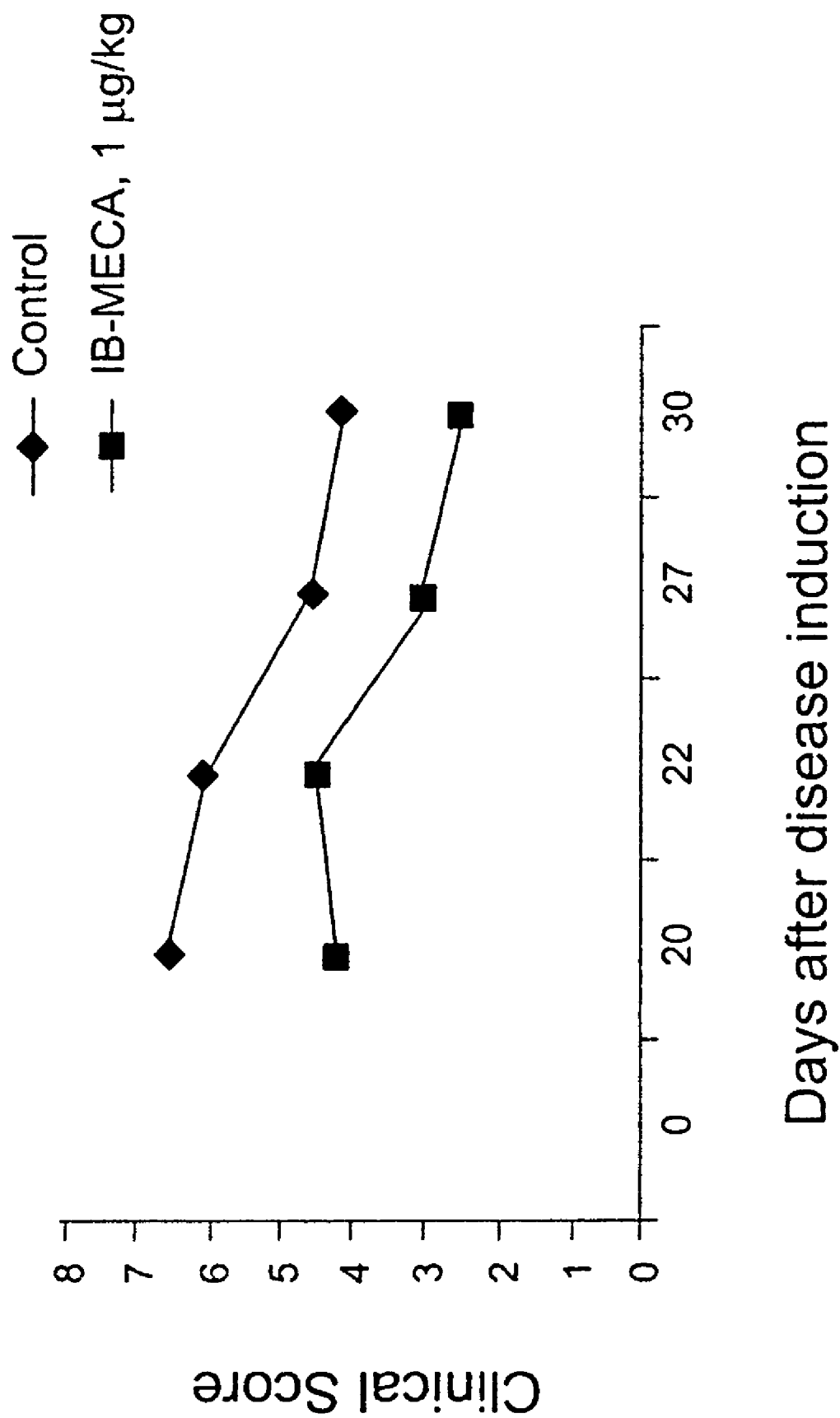
FIG. 1B: shows the effect of PO administered IB-MECA 1 microgram/Kg a day (square), or control untreated mice (diamond), on the inflammatory intensity in an animal model of adjuvant arthritis.
Figure 2A:
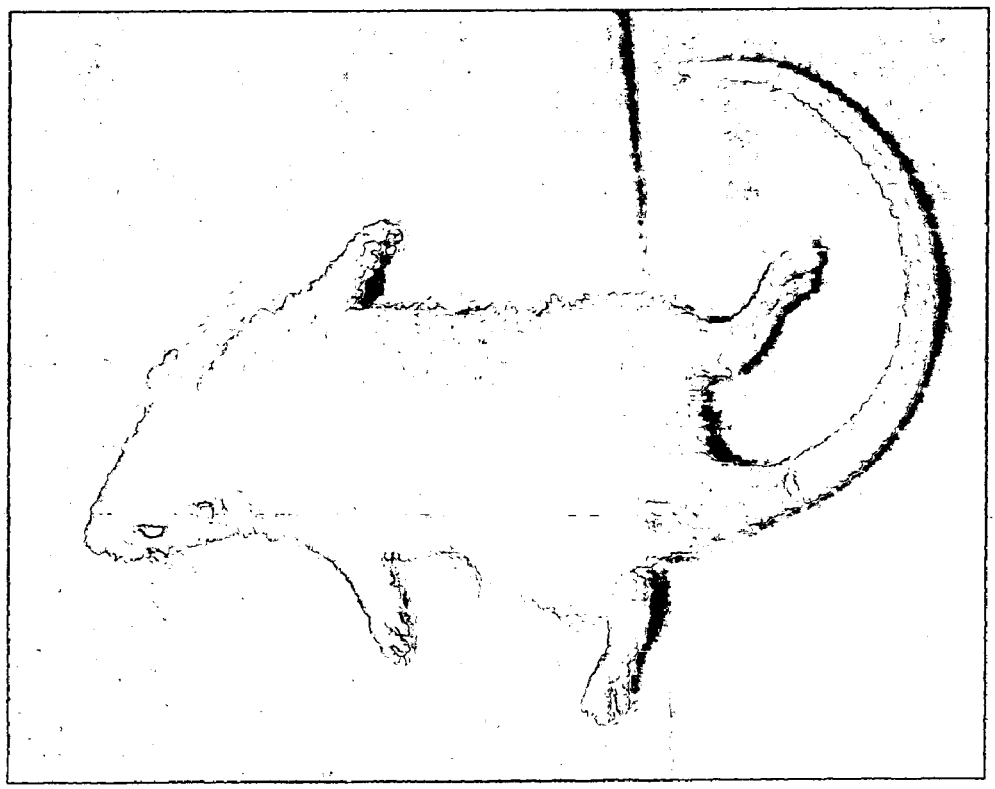
FIGS. 2A and 2B: show pictures of rats of FIG. 1, having adjuvant induced arthritis, untreated (2A) and treated with 10 microgram/kg a day IB-MECA (treatment starts 7 days after disease induction (2B))
Figure 2B:
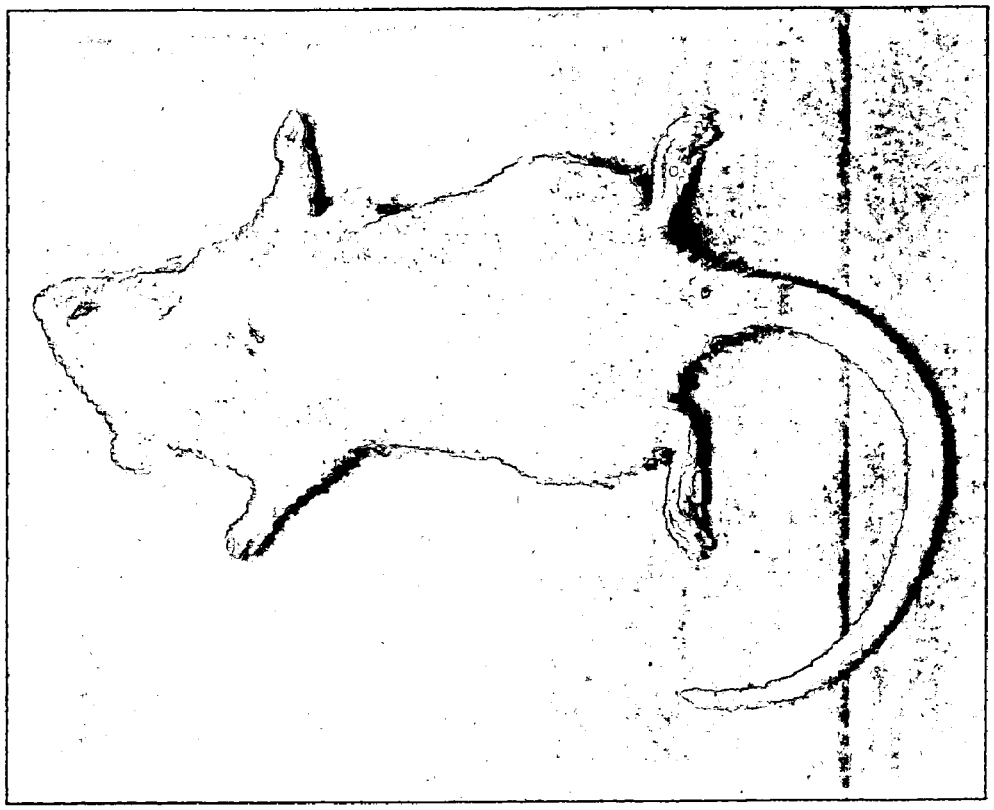

Rats were induced with adjuvant arthritis as described above. Animals were divided into three groups each consisting of 10 rats. Group 1 served as control while group 2 was administered with 100 µg/kg PO IB-MCA a day, and group 3 was administered with 10 µg/kg PO IB-MECA a day. Treatment with the active substance began 7 days disease induction. The results are shown in FIG. 1A. As can be seen, administration of 100 µg/kg or 10 µg/kg a day was effective in abolishing almost completely the inflammation as assessed by the inflammation intensity score. FIG. 1B shows the same experiment repeated with 1 µg/day. As can be seen even in this low dose a significant reduction was evident. FIGS. 2A and 2B show pictures of a control untreated rat induced with adjuvant arthritis (2A) and a rat treated with 10 µg/kg a day IB-MECA (2B). As can be seen while the paws of the untreated rat appear extremely swollen and red, the treated animal featured normal appearing paws.

FIGS. 3A and 3B show histological pictures of the joint of an untreated rat (3A), featuring the typical arthritis destruction of the synovial tissue and bone.

Against this the histological picture (3B) of adjuvant arthritis induced rat treated with 10 µg a day of IB-MECA appeared completely normal without featuring any destructive processes.

Example 1B

Effect of 10 and 100 µg/kg Cl-IB-MECA on Arthritis Score-Adjuvant Model

Figure 4:
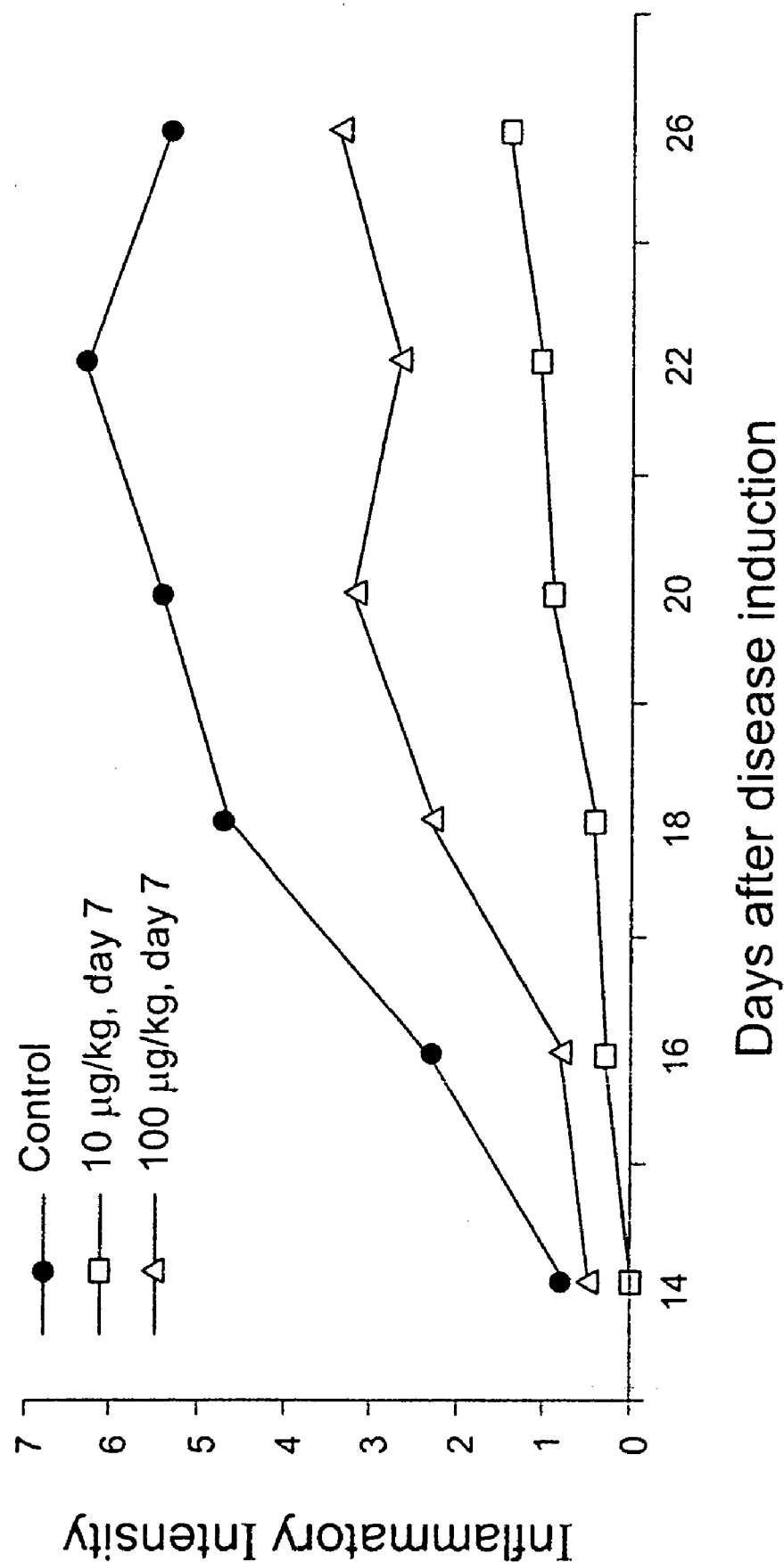
FIG. 4: shows inflammatory intensity in a model of adjuvant arthritis as a function of time for control untreated rats (dark circles); rats treated with 10 microgram/kg a day Cl-IB-MECA (squares) and rats treated with 100 microgram/kg a day of Cl-IB-MECA (triangles); treatment started 7 days after disease induction.

Rats were induced with adjuvant arthritis as described above. Rats were divided to tree groups each consisting of 10 animals. Group 1 served as control while group 2 was administered with 100 µg/kg PO Cl-IB-MECA a day, and group 3 was administered with 10 µg/kg CL-IB-MECA PO a day. Administration was initiated at day 7 after disease induction. The results are shown in FIG. 4.

As can be seen administration of 10 µg a day was significantly more effective in improving the arthritis score than administration of 100 µg/kg a day indicating that surprisingly the active ingredient does not have a classic "dose response effect" wherein the higher the dosage the more pronounced the effect, but rather a bell-shaped curve effect, where increase in the dosage caused decrease in the therapeutical effect. FIGS. 5A to 5D show photographs of a control untreated rat induced with adjuvant arthritis (5A) and a rat treated with 10 µg/kg a day-CL-IB-MECA (5C). While the paws of the untreated rat appear extremely swollen and red, the treated animal featured normal appearing paws.

Example 1C

Effect of 10 µg/kg IB-MECA on Joint Swelling and Histology Score-collagen Induced Model in Mice Male DBA mice were treated to produce collagen-induced-arthritis as described above. Each group contained 10 animals and each experiment was conducted at least three times.

IB-MECA (10 µg/kg) was orally administered by gavage, twice daily starting at onset of clinical arthritis. The positive control received vehicle only. The inflammatory intensity in the CIA model was determined in accordance with the increase in the mice hind paw's diameter, measured by caliper (Mitotoyo, Tokyo, Japan). The mean score in each experimental group was designated as the "Clinical Score".

Histology Score

Animals were sacrificed, the legs were removed up to the knees level, fixed in 10% formaldehyde, decalcified, dehydrated, paraffin-embedded, cut into 4 µm sections and stained by Hematoxylin-Eosin.

The assessment of all pathologic findings were performed blind (by L. R-W and M. H) using semi-quantitative grading scales of 0 to 4 for the following parameters:

a) The extent of inflammatory cells' infiltration to the joint tissues, b) Synovial lining cell hyperplasia, c) Pannus formation, d) Joint cartilage layers destruction, e) Bone damage and erosion score was graded 0–5:
0—normal.

1—minimal loss of cortical bone at a few sites; 2—mild loss of cortical trabecular bone; 3—moderate loss of bone at many sites; 4—marked loss of bone at many sites; 5—marked loss of bone at many sites with fragmenting and full thickness penetration of inflammatory process or pannus into the cortical bone (17,18). The mean of all the histological parameters scores were designated "Histology Score".

Results

Figure 6:
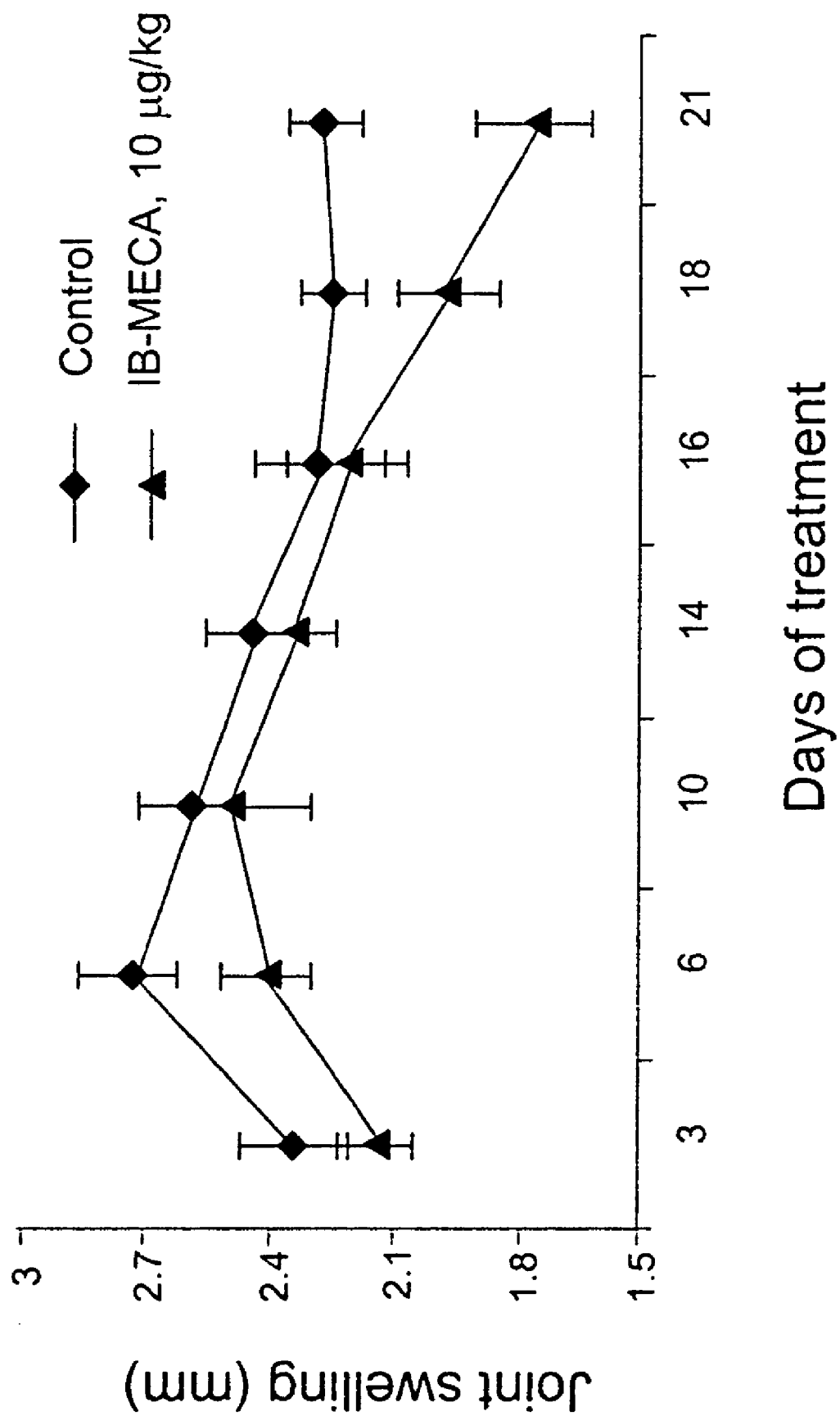
FIG. 6: shows the effect of administration of 10 microgram/kg of IB-MECA (CF-101) on joint swelling in a collagen-induced-arthritis (CIA) model in mice.
Figure 7:
FIG. 7A: shows a histological section of joints of normal mice.
FIG. 7B: shows histological cross section of joints of untreated collagen-induced-arthritic mice.
FIG. 7C: shows histological cross section of collagen-induced-arthritic mice treated with 10 μg/kg IB-MECA.
Figure 8:
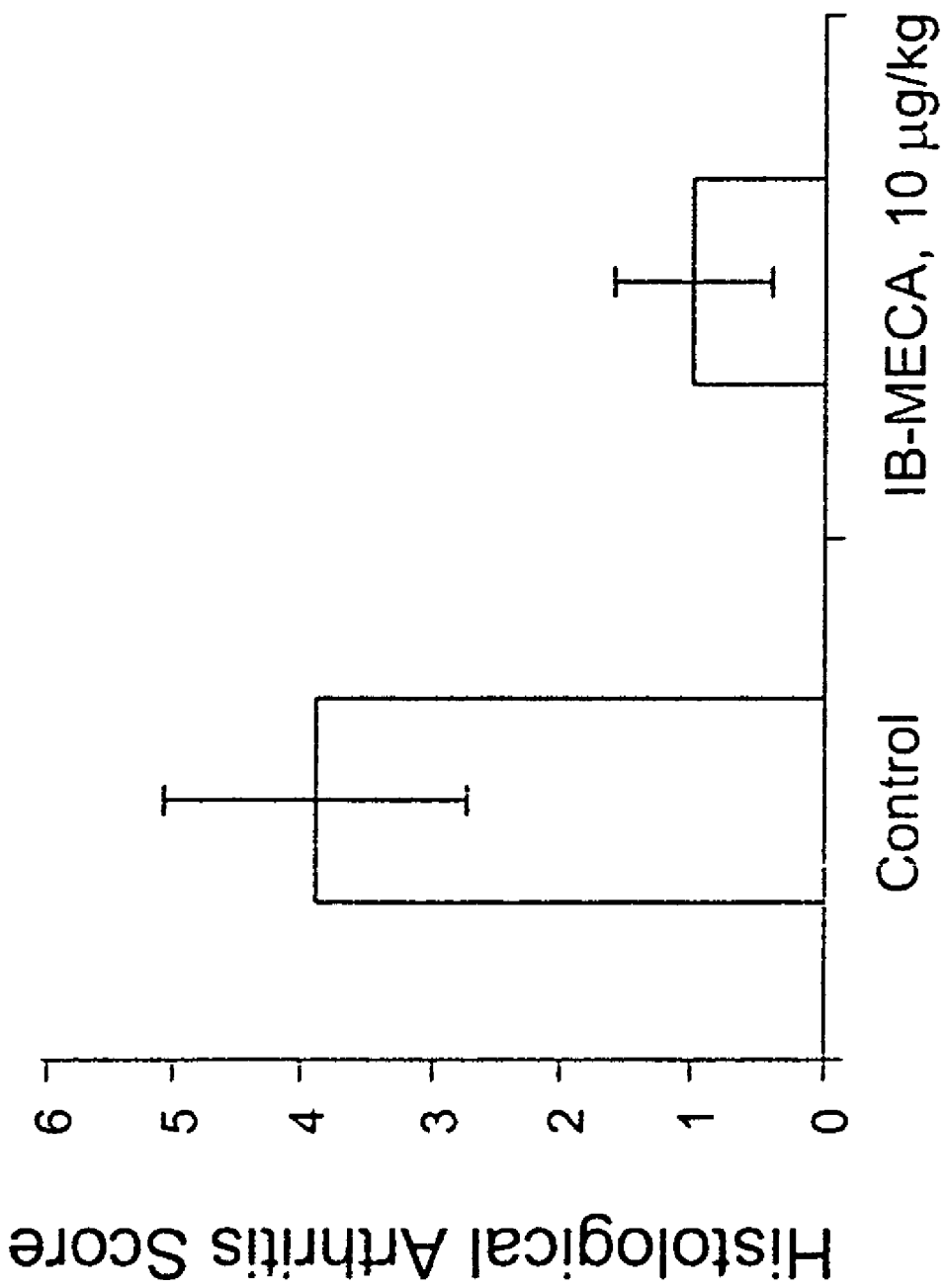
FIG. 8: shows a combined histological score of CIA mice not treated (control) and CIA mice treated with 10 microgram/kg of IB-MECA.

In the following experiments, the effect of IB-MECA (10 µg/kg/day) on the development of collagen-induced arthritis was evaluated. The mice developed the disease several days after the second immunization with Type II collagen/CFA emulsion. In each individual mouse, IB-MECA was administered at the onset of disease. In the control group a maximal hind paw swelling was observed 6 days after disease onset, whereas in the IB-MECA treated group it was noted on day 14th (FIG. 6). The intensity of the arthritis was reduced throughout the experimental period, but on day 21 this difference became statistically significant (p<0.02). In the IB-MECA treated group (FIG. 7C) histology sections showed minimal inflammatory changes compared to the extensive one in the control group (FIG. 7A) and a pattern that was similar to control (FIG. 7B). In addition, the histology score was markedly lower in the IB-MECA treated group compared to the control group (3.87±1.2 vs. 1.0±0.6, p<0.01) (FIG. 8).

Example 1D

Clinical Trial in Humans—Effect of IB-MECA on Rheumatoid Arthritis

Patients with active rheumatoid arthritis were chosen for the study. All chosen patients met the following criteria:

Inclusion Criteria

Rheumatoid arthritis patients that were included in the study, met the following inclusion criteria:

1. Males and females 18 years of age or older
2. Functional Class I, II, or III by the criteria of the American College of Rheumatology
3. Active RA, as indicated by the presence of (a) ≧6 swollen joints; AND (b) ≧29 tender joints; AND at least one of he following: (c) Westergren ESR of ≧28 mm/hour; OR (d) CRP level of >2.0 mg/dL; OR (e) morning stiffness for >45 minutes 4. History of unsuccessful treatment (documented intolerance or lack of efficacy as determined by the Investigator) with at least 1, but no more than 4, of the following disease modifying anti-rheumatic drugs (DMARDs): methotrexate, hydroxychloroquine, sulfasalazine, oral or injectable gold, azathioprine, leflunomide, minocycline, and penicillamine, alone or in combination Protocol Patients included in the study were subjected to a 1 month washout period in which they ceased to take any DMARD. Following this one months washout the patients were administered twice daily with either with 0.1 mg, 1 mg of 4 mg of IB-MECA in a double-blind fashion. The drug was formulated in a soft gel capsule containing IB-MECA dissolved in Cremophor RH. The patients received the drug for a period of up to 12 weeks.

Clinical Assessment

Disease activity was assessed using standard criteria as laid down by the American College of Rheumatology (ACR).

Results 15 patients were treated and in at least half of them a significant improvement in disease symptoms was observed for a period of up to the 12 weeks of the study.

EXAMPLE 2

Determining Maximal Tolerated Dose of IB-MECA in Humans

Methods

Study design

Two clinical studies were carried out: a single dose study and a repeat dose study. Both studies were parallel-group, double-blind, dose-rising, and placebo-controlled in design.

In the single dose study, 15 healthy men (3 groups of 5) received a single oral dose of IB-MECA (1, 5 or 10 mg) or placebo. In each group, 1 subject received placebo. In the repeated dose study, 28 healthy men (4 groups of 7) received repeated oral doses of IB-MECA (2, 3, 4 or 5 mg) or placebo every 12 h for 7 days. In each group, 2 subjects received placebo.

Selection of Subjects

Healthy young men, aged 18–45 years.

Study Drugs

In the single dose study, a solution with IB-MECA powder in 30% Cremophor RH40 (BASF) was used. In the repeated dose study, an aqueous 0.5% methylcellulose suspension (Methocel A4M Premium, The Dow Chemical Company) was used. In both studies, the study medication was taken orally as a drink, followed by 50 ml of tap water.

Study Procedures

The following procedures were done:

Safety assesment: laboratory assessments (routine biochemistry and urinalysis), physical examination, 12-lead ECG, ambulatory ECG, pulmonary function testing (FEV1), vital signs (semi-recumbent in the single dose study; semi-recumbent and standing in the repeat dose study). Adverse events were recorded throughout both studies.

Determination of IB-MECA blood level: in the single dose study blood samples for assay of IB-MECA were taken immediately before and at 0.25, 0.5, 1, 2, 4, 8, 12, 24, and 48 h after dosing; in the repeat dose study—blood samples were taken immediately before and at 0.25, 0.5, 1, 2, 4, 8, and 12 h after dosing on Day 1, before dosing on Days 2–6, and before and at 0.25, 0.5, 1, 2, 4, 8, 12, and 24 h after dosing on Day 7.

Plasma samples were assayed for IB-MECA using LC/MS/MS. The lower limit of quantification (LLOQ) was 0.1 ng/mL. Intra-assay coefficients of variation (CV) were <5.0% and inter-assay CVs were <9.4%.

Pharmacokinetic Analysis

Maximum concentration ($C_{max}$) and time to maximum concentration ($t_{max}$) were observed values. Other pharmacokinetic parameters (half-life, $t^{1/2}$; AUC; and clearance, CL/F) were calculated by non-compartmental methods using WinNonlin® software (version 3.0, Pharsight, Mountain View, Calif., US). Accumulation indices of $C_{max}$ and AUC were calculated as ratio of values at steady state (Day 7) to the values on Day 1.

Statistical Analysis

Data from all subjects who received IB-MECA were included in the analysis of safety and tolerability (adverse events and laboratory safety variables). Numerical data and parameters were summarised using means or medians, and other descriptive statistics, according to the type and distribution of the data.

Results

Study population

In the single dose study, the mean (range) age, weight, and height were 28.3 (20–40 years, 75.9 (63–98) kg, and 177.8 (167–188) cm, respectively. In the repeat dose study, the mean (range) age, weight, and height were 25.2 (18–45) years, 75.3 (56–99) kg, and 178.0 (163–189) cm, respectively. All volunteers were of Europid ethnic origin, except for 2 Asian/Indian men and 1 Europid/Oriental man.

All subjects were deemed healthy at screening, without any haematological disorder or history of splenectomy, nor splenomegaly on physical examination.

Safety and tolerability

Figure 9:
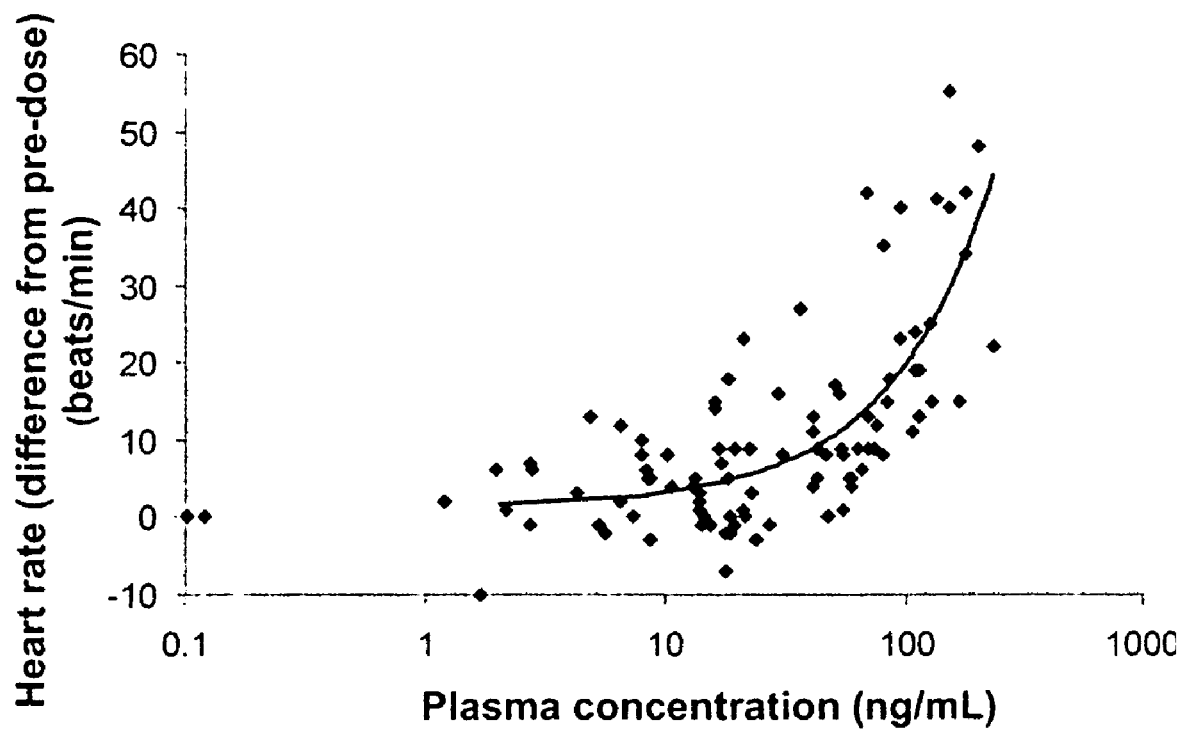
FIG. 9: shows the change in semi-recumbent heart rate as a function of plasma IB-MECA concentration after single doses of IB-MECA.

In the single dose study, IB-MECA in doses up to 5 mg was well tolerated, as judged by vital signs, physical examination, FEV1, and 12-lead and continuous ECG. There were no clinically significant changes in safety tests of blood and urine. Four subjects had a small increase in resting heart rate after 5 mg IB-MECA; however, after the 10 mg dose, 4 subjects had substantial increases in resting heart rate, 2 of which were substantial (up to 115 beats/min) and considered drag-related. Those 2 subjects developed nausea, and 1 of them vomited once and was facially flushed. Those changes precluded our studying higher doses. In no subject was there a significant change in blood pressure, but blood pressure was not measured in the standing position. The increase in heart rate was closely related to the plasma IB-MECA concentration (FIG. 9).

Figures 10A, 10B:
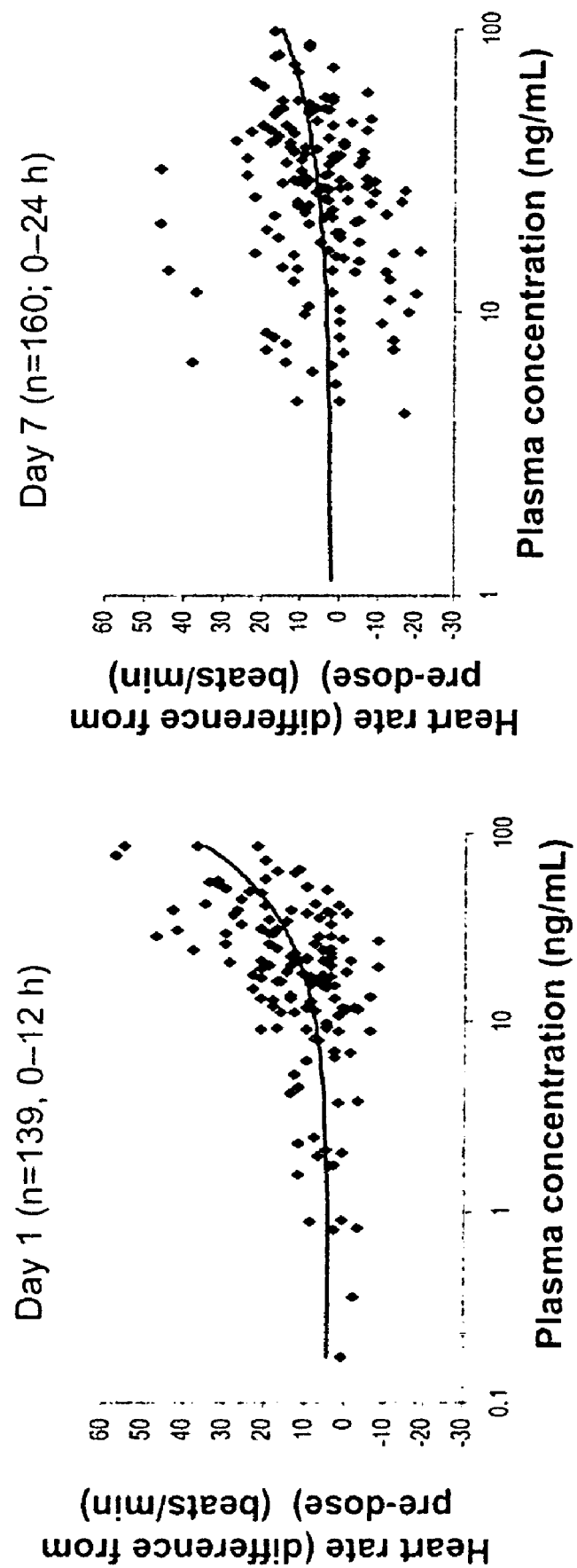
FIGS. 10A and 10B: show the change in standing heart rate as a function of plasma IB-MECA concentration after repeated doses of IB-MECA.

In the repeat dose study, IB-MECA had an acceptable safety profile, as judged by vital signs, physical examination, FEV1, and 12-lead and continuous ECG. There was a dose-related increase in heart rate on Day 1, but some tolerance developed, because that effect was clearly smaller on Day 7. On Day 1, the time course of the increase in heart rate reflected the profile of plasma IB-MECA concentrations. However, on Day 7, equivalent plasma IB-MECA concentrations were associated with smaller increases in heart rate (FIGS. 10A & 10B). There, were no clinically significant changes in safety tests of blood and urine.

Most of the adverse events occurred during the 5 mg dose regimen: headache and drowsiness were most common. Two adverse events were vascular disorders—hot flushes and dizziness on standing.

Overall, IB-MECA was well tolerated at single doses of up to 5 mg and repeat doses of up to 4 mg 12-hourly. Adverse events were related to dose and generally occurred around the time of maximal blood concentration ($t_{max}$). After single doses of up to 5 mg IB-MECA, there were no adverse events within 12 h of dosing, but after a single dose of 10 mg, there were 8 adverse events within 12 h of dosing. After repeated doses of up to 4 mg 12-hourly, there were 2 adverse events within 12 h of dosing. However, after repeated doses of 5 mg 12-hourly, there were 13 adverse events within 12 h of dosing. Thus, based on this repeat dose study, the 4 mg dose was determined to be the maximum tolerated dose for a twice-daily therapeutic regimen.

Overall a single daily dose of 5 mg and a twice daily dose of 4 mg where considered safe and well tolerated. Given the fact that these doses gave a plasma level (Cmax) of less than 160 nM (80 ng/ml)

Pharmacokinetics

The pharmacokinetics of single doses of IB-MECA are shown in the following Table 1:

TABLE 1

Mean (SD) plasma PK parameters after a single oral dose of CF101 (n = 4 per group)

| Dose (mg) | $C_{max}$ (ng/mL) | $t_{max}$[a] (h) | $AUC_{(0-48)}$ (ng · h/mL) | $AUC_{(inf)}$ (ng · h/mL) | $t_{1/2}$ (h) | CL/F (L/h) |
|---|---|---|---|---|---|---|
| 1 | 21.2 (2.1) | 1 (1–2) | 220.7 (20.9) | 225.2 (21.7) | 8.7 (0.7) | 4.5 (0.4) |
| 5 | 81.6 (23.6) | 1 (1–2) | 872.3 (211.6) | 904.0 (221.9) | 8.3 (0.2) | 5.8 (1.4) |
| 10 | 178.0 (46.6) | 1 (1–2) | 1780.0 (228.7) | 1813.0 (226.5) | 8.6 (0.4) | 5.6 (0.7) |

[a]median (range)

As can be seen, IB-MECA pharmacokinetics were linear, and inter-subject variability was low. IB-MECA was absorbed rapidly: $t_{max}$ ranged between 1–2 h. Mean $C_{max}$ (maxim plasma level) and $AUC_{0-48}$ (area under the cure of blood level over 48 hours after administration) were related to dose. $C_{max}$ was 21.2, 81.6, and 178.0 ng/ml, and $AUC_{0-48}$ was 220.7, 872.3, and 1780.0 ng.h/ml, for doses of 1, 5, and 10 mg, respectively. The half-life of about 8.5 h was independent of dose. Apparent plasma clearance (CL/F) was low (4–7 L/h) and independent of dose.

The pharmacokinetics of repeated doses of IB-MECA are shown in the following Table 2:

TABLE 2

Mean (SD) plasma PK parameters on Days 1 and 7 of repeated dosing with CF101 (n = 5 per group)

| Dose (mg) | Day | $C_{max}$ (ng/mL) | $t_{max}$[a] (h) | $AUC_{(0-12)}$ (ng · h/mL) | $AUC$[b] (ng · h/mL) | $t_{1/2}$ (h) | CL/F (L/h) |
|---|---|---|---|---|---|---|---|
| 2 | 1 | 22.0 (3.3) | 2 (1–4) | 155.2 (39.1) | 207.4 (52.0) | 5.52 (0.2) | 10.1 (2.3) |
|   | 7 | 30.9 (3.1) | 2 (1–2) | 242.4 (41.4) | 346.3 (64.0) | 9.83 (1.2) | 4.9 (0.7) |
| 3 | 1 | 49.3 (9.7) | 2 (1–2) | 304.5 (19.5) | 423.5 (27.5) | 6.29 (1.0) | 7.1 (0.5) |
|   | 7 | 49.0 (7.9) | 1 (1–2) | 341.6 (38.1) | 512.1 (74.1) | 9.25 (0.8) | 5.0 (0.6) |
| 4 | 1 | 46.2 (11.4) | 2 (1–2) | 297.0 (57.2) | 400.2 (85.7) | 5.77 (0.6) | 10.4 (2.1) |
|   | 7 | 58.1 (10.4) | 1 (1–2) | 458.3 (54.8) | 640.3 (73.7) | 8.93 (0.8) | 5.4 (0.7) |
| 5 | 1 | 63.6 (22.0) | 2 (1–2) | 461.6 (157.4) | 596.1 (196.6) | 4.96 (0.3) | 9.3 (3.5) |
|   | 7 | 79.5 (24.1) | 2 (2–2) | 601.0 (163.6) | 818.4 (214.0) | 9.39 (0.6) | 5.4 (1.5) |

[a]median (range)
[b]$AUC_{(inf)}$ on Day 1, $AUC_{(0-24)}$ on Day 7

IB-MECA was absorbed rapidly: $t_{max}$ was 1–2 h. Steady state was reached by Day 3. IB-MECA pharmacokinetics did not change after repeated dosing. Plasma concentrations of IB-MECA were dose proportional on Day 1 and at steady state (Day 7). Half-life of IB-MECA was independent of dose, and was about 9–10 h at steady state. As in the single dose study, apparent plasma clearance (CL/F) was low (5–10 L/h) and independent of dose. The accumulation indices ranged between 1–1.4 and 1.1–1.6 for $C_{max}$ and AUC, respectively; the accumulation indices were much as predicted from the single dose data.

SUMMARY

Overall a single daily dose of 5 mg and a twice daily dose of 4 mg where considered safe and well tolerated. Given the fact that. These doses gave a $C_{max}$ of less than about 160 nM (80 ng/ml).

The invention claimed is:

1. A method for the treatment of inflammatory arthritis (IA) in a human subject, comprising: orally administering to an individual in need of such treatment an effective amount of an active agent consisting of $N^6$-(3-iodobenzyl)-adenosine-5'-N-methyl-uronamide (IB-MECA) or 2-chloro-$N^6$-(3-iodobenzyl)-adenosine-5'-N-methyl-uronamide (Cl-IB-MECA; wherein the effective amount is an amount which is less than about 70 microgram/Kg.

2. A method of claim 1, wherein the active agent is administered once a day at a dose of less than about 5 mg.

3. A method of claim 1, wherein the active agent is administered twice a day.

4. A method for the treatment of inflammatory arthritis (IA) in a human subject, comprising orally administering to an individual in need of such treatment an effective amount of $N^6$-(3-iodobenzyl)-adenosine-5'-N-methyl-uronamide (IB-MECA) or 2-chloro-$N^6$-(3-iodobenzyl) -adenosine-5'-N-methyl-uronamide (Cl-IB-MECA), wherein the effective amount is a dose of about 0.1 to 1.5 mg administered once or twice per day.

* * * * *